(12) United States Patent
Alfonso et al.

(10) Patent No.: US 12,350,487 B2
(45) Date of Patent: Jul. 8, 2025

(54) METHODS FOR FABRICATING SEGMENTED ELECTRODES

(71) Applicant: Advanced Neuromodulation Systems, Inc., Plano, TX (US)

(72) Inventors: Ted Alfonso, Frisco, TX (US); Steve Wheeler, Duncanville, TX (US); Jeff Urbanski, Frisco, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 601 days.

(21) Appl. No.: 17/673,157

(22) Filed: Feb. 16, 2022

(65) Prior Publication Data

US 2023/0256235 A1    Aug. 17, 2023

(51) Int. Cl.
| | |
|---|---|
| B23P 13/00 | (2006.01) |
| A61N 1/05 | (2006.01) |
| B21D 22/02 | (2006.01) |
| B21D 35/00 | (2006.01) |
| B23P 11/00 | (2006.01) |
| H01R 43/16 | (2006.01) |
| A61N 1/36 | (2006.01) |

(52) U.S. Cl.
CPC .............. *A61N 1/05* (2013.01); *B21D 22/025* (2013.01); *B21D 35/002* (2013.01); *B23P 11/00* (2013.01); *B23P 13/00* (2013.01); *H01R 43/16* (2013.01); *A61N 1/36125* (2013.01); *Y10T 29/49222* (2015.01)

(58) Field of Classification Search
CPC .......... B23P 13/00; B23P 15/00; H01R 43/16; Y10T 29/49222
USPC ........................................... 29/884, 825, 874
See application file for complete search history.

(56) References Cited

U.S. PATENT DOCUMENTS

| | | | |
|---|---|---|---|
| 8,321,025 B2 | 11/2012 | Bedenbaugh | |
| 8,700,179 B2 | 4/2014 | Pianca et al. | |
| 9,295,830 B2 | 3/2016 | Pianca | |
| 10,786,679 B2 | 9/2020 | Reddy | |
| 2012/0203321 A1* | 8/2012 | Moffitt | A61N 1/0534 607/148 |
| 2016/0114151 A1 | 4/2016 | Sommer et al. | |

FOREIGN PATENT DOCUMENTS

JP            4308528        *   8/2009

* cited by examiner

*Primary Examiner* — Thiem D Phan
(74) *Attorney, Agent, or Firm* — Armstrong Teasdale LLP

(57) ABSTRACT

A method for fabricating a segmented electrode is provided. The method includes performing a series of progressive die stamping operations on a foil sheet of material to form an initial electrode, and removing portions of the initial electrode using a centerless grinding process to form a segmented electrode including a plurality of circumferentially spaced contacts.

24 Claims, 6 Drawing Sheets

METHODS FOR FABRICATING SEGMENTED ELECTRODES

A. FIELD OF THE DISCLOSURE

The present disclosure relates generally to electrode assemblies, and more particularly to fabricating segmented electrodes.

B. BACKGROUND ART

Neurostimulation systems are devices that generate electrical pulses and deliver the pulses to nerve tissue to treat a variety of disorders. Spinal cord stimulation (SCS) is an example of neurostimulation in which electrical pulses are delivered to nerve tissue in the spine for the purpose of chronic pain control. Other examples include deep brain stimulation (DBS), cortical stimulation, cochlear nerve stimulation, peripheral nerve stimulation, vagal nerve stimulation, sacral nerve stimulation, etc.

Neurostimulation systems and other medical device systems may include segmented electrodes (i.e., electrodes that include a plurality of circumferentially spaced contacts). In at least some known existing systems, segmented electrodes are manufactured by breaking a tubular electrode into multiple segments. This process, however, may be time-consuming and expensive, and may result in wasted material. Accordingly, a faster, more cost-effective method for manufacturing segmented electrodes is desirable.

BRIEF SUMMARY OF THE DISCLOSURE

In one aspect, a method for fabricating a segmented electrode is provided. The method includes performing a series of progressive die stamping operations on a foil sheet of material to form an initial electrode, and removing portions of the initial electrode using a centerless grinding process to form a segmented electrode including a plurality of circumferentially spaced contacts.

In another aspect, a method of forming an electrode assembly is provided. The method includes performing a series of progressive die stamping operations on a foil sheet of material to form an initial electrode, coupling the initial electrode to a lead body, and removing portions of the initial electrode using a centerless grinding process to form a segmented electrode on the lead body, the segmented electrode including a plurality of circumferentially spaced contacts.

In yet another aspect, a method of forming an implantable stimulation lead is provided. The method includes performing a series of progressive die stamping operations on a foil sheet of material to form an initial electrode, coupling the initial electrode to a lead body, removing portions of the initial electrode using a centerless grinding process to form a segmented electrode on the lead body, the segmented electrode including a plurality of circumferentially spaced contacts, and electrically connecting each of the plurality of circumferentially spaced contacts to associated conductors of the lead body to form the implantable stimulation lead.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

Figure 1:
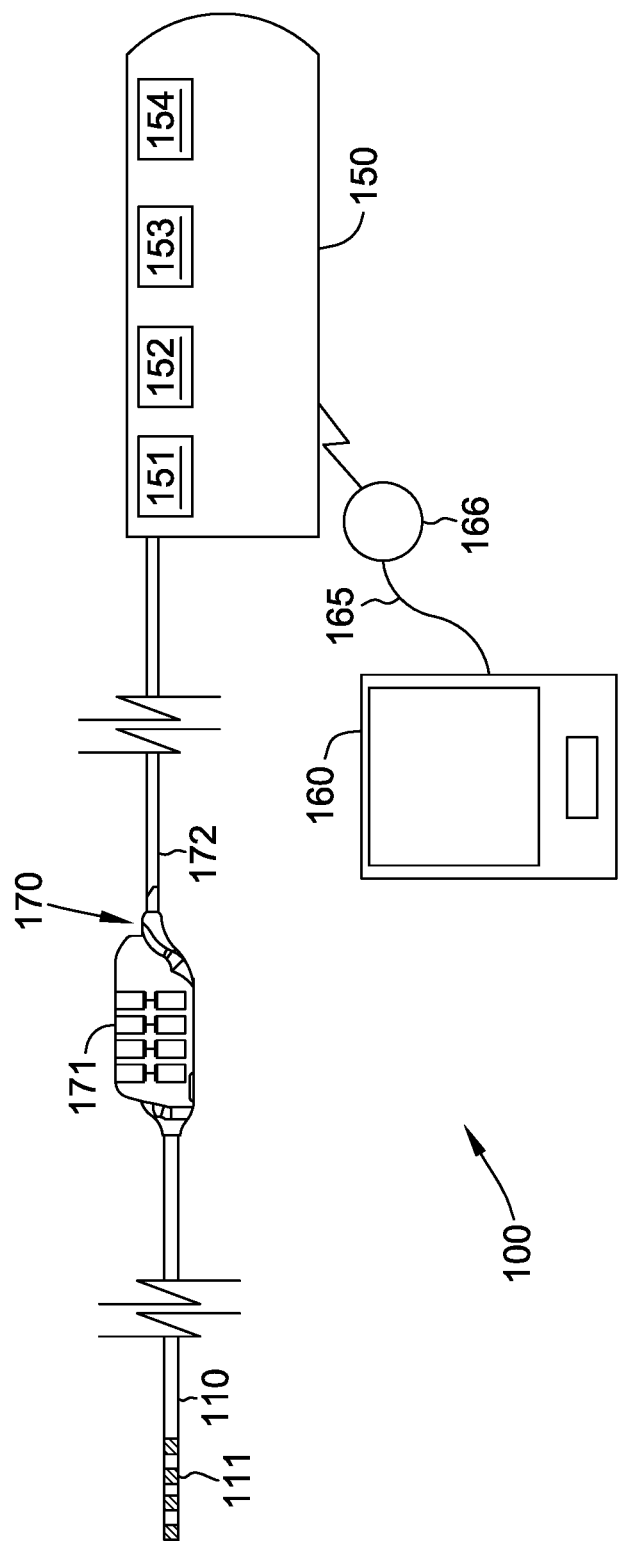
FIG. 1 is a schematic view of one embodiment of a stimulation system.

The present disclosure provides systems and methods for fabricating a segmented electrode is provided. A method includes performing a series of progressive die stamping operations on a foil sheet of material to form an initial electrode, and removing portions of the initial electrode using a centerless grinding process to form a segmented electrode including a plurality of circumferentially spaced contacts.

In the description herein for embodiments of the present disclosure, numerous specific details are provided, such as examples of circuits, devices, components, and/or methods, etc., to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an electrical element, component or module may be configured to perform a function if the element may be programmed for performing or otherwise structurally arranged to perform that function.

Neurostimulation systems are devices that generate electrical pulses and deliver the pulses to nerve tissue of a patient to treat a variety of disorders. One category of neurostimulation systems is DBS. In DBS, electrical pulses are delivered to parts of a subject's brain, for example, for the treatment of movement and effective disorders such as PD and essential tremor.

Neurostimulation systems generally include a pulse generator and one or more leads. A stimulation lead includes a lead body of insulative material that encloses wire conductors. The distal end of the stimulation lead includes multiple electrodes, or contacts, that are electrically coupled to the wire conductors. The proximal end of the lead body includes multiple terminals (also electrically coupled to the wire conductors) that are adapted to receive electrical pulses. In DBS systems, the stimulation lead is implanted within the brain tissue to deliver the electrical pulses. The stimulation leads are then tunneled to another location within the patient's body to be electrically connected with a pulse generator or, alternatively, to an "extension." The pulse generator is typically implanted within a subcutaneous pocket created during the implantation procedure.

The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

Although the systems and methods disclosed herein are described in the context of a neurostimulation system, and in particular a DBS system, those of skill in the art will appreciate that the electrode fabrication techniques may be implemented in applications other than neurostimulation systems. For example, the embodiments described herein may be used to fabricate sensing or stimulation electrodes in a variety of medical devices.

Referring now to the drawings, and in particular to FIG. 1, a stimulation system is indicated generally at 100. Stimulation system 100 generates electrical pulses for application to tissue of a patient, or subject, according to one embodiment. System 100 includes an implantable pulse generator (IPG) 150 that is adapted to generate electrical pulses for application to tissue of a patient. IPG 150 typically includes a metallic housing that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of IPG 150 for execution by the microcontroller or processor to control the various components of the device.

IPG 150 may include one or more attached extension components 170 or be connected to one or more separate extension components 170. Alternatively, one or more stimulation leads 110 may be connected directly to IPG 150. Within IPG 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from IPG 150 and conducted through the conductors of lead body 172 are provided to stimulation lead 110. The pulses are then conducted through the conductors of lead 110 and applied to tissue of a patient via electrodes 111. Any suitable known or later developed design may be employed for connector portion 171.

For implementation of the components within IPG 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within IPG 150. Different pulses on different electrodes may be generated using a single set of pulse generating circuitry using consecutively generated pulses according to a "multi-stim set program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may include a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number and type of electrodes 111, terminals, and internal conductors.

Controller device 160 may be implemented to recharge battery 153 of IPG 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller device 160 generates an AC-signal to drive current through coil 166 of wand 165. Assuming that primary coil 166 and secondary coil are suitably positioned relative to each other, the secondary coil is disposed within the field generated by the current driven through primary coil 166. Current is then induced in secondary coil. The current induced in the coil of the implantable pulse generator is rectified and regulated to recharge battery of IPG 150. The charging circuitry may also communicate status messages to controller device 160 during charging operations using pulse-loading or any other suitable technique. For example, controller device 160 may communicate the coupling status, charging status, charge completion status, etc.

External controller device 160 is also a device that permits the operations of IPG 150 to be controlled by user after IPG 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 150.

Controller device 160 preferably provides one or more user interfaces to allow the user to operate IPG 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stim set during execution of program), etc. In the methods and systems described herein, parameters may include, for example, a number of pulses in a burst (e.g., 3, 4, or 5 pulses per burst), an intra-burst frequency (e.g., 130 Hz), an inter-burst frequency (e.g., 3-20 Hz), and a delay between a first and second burst.

IPG 150 modifies its internal parameters in response to the control signals from controller device 160 to vary the stimulation characteristics of stimulation pulses transmitted through stimulation lead 110 to the tissue of the patient. Neurostimulation systems, stim sets, and multi-stim set programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference. Example commercially available neurostimulation systems include the EON MINI™ pulse generator and RAPID PROGRAMMER™ device from Abbott Laboratories.

Figure 2:
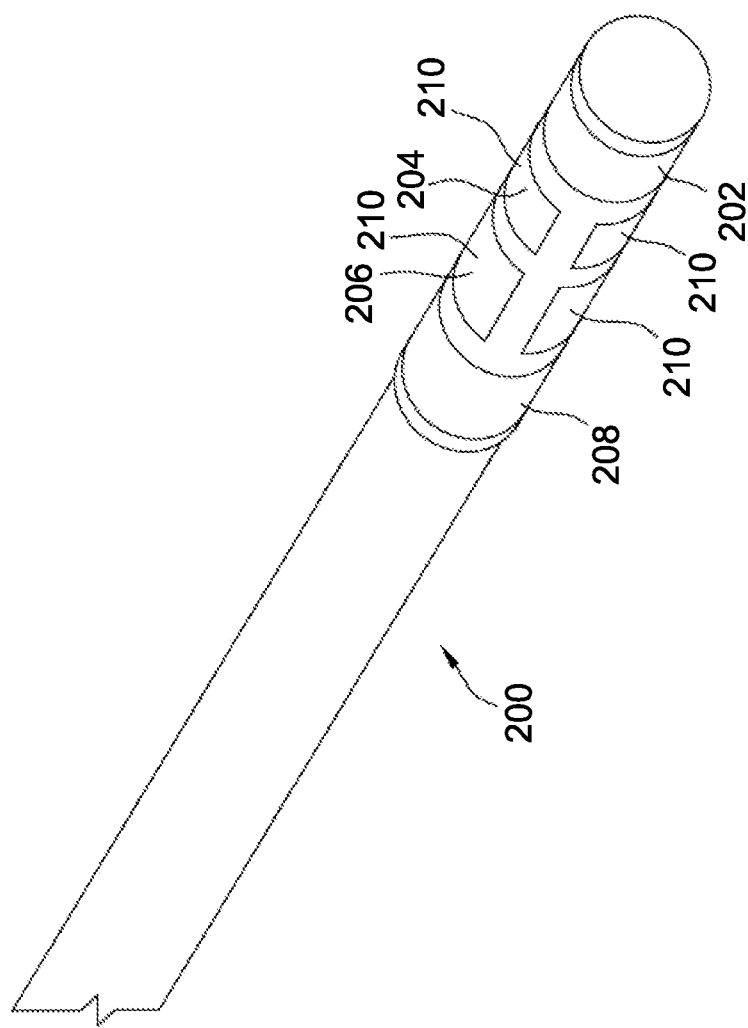
FIG. 2 is a perspective view of one embodiment of a lead that may be used with the stimulation system shown in FIG. 1.

FIG. 2 is a perspective view of a DBS lead 200 that may be used to implement the systems and methods described herein. DBS lead 200 includes a first electrode 202, a second electrode 204, a third electrode 206, and a fourth electrode 208 In this embodiment, first electrode 202 and fourth electrode 208 are both ring electrodes. Further, second electrode 204 is a segmented electrode includes three contacts 210 (two of which are shown in FIG. 2), and third electrode 206 is a segmented electrode including three contacts 210 (two of which are shown in FIG. 2). Those of skill in the art will appreciate that DBS lead 200 may have any suitable electrode configuration, and that the electrode configuration shown in FIG. 2 is merely an example.

In at least some known systems, segmented electrodes are formed by producing an initial electrode using electrical discharge machining (EDM) or a combination of EDM and traditional metal machining, and then segmenting that initial electrode using centerless grinding. Although these processes can be used to generate electrodes with small features, the manufacturing cost is relatively high.

For example, the electrode is typically made from a platinum-iridium (Pt/Ir) alloy, which is an expensive precious metal. Alternatively, the electrode may be made of a different alloy, pure platinum, or any suitable material. Grooves that enable segmenting and thin tabs that enable anchoring are generated while attempting to minimize scrap. In one known method, extruded Pt/Ir tubing is cut to a desired length, and the tubular electrode is broken circumferentially into segments. To attach these segments onto a round polymer lead body, anchoring features are used to retain the segments on the lead body.

These anchoring features may be thin flanges that protrude from proximal and distal ends of the segments, and that have a smaller outer diameter than the face of the segments. To anchor the segments to the lead body, the polymer from the lead body can be flowed over the flanges. It may be challenging to position the electrode segments uniformly around the circumference of the lead body and hold them in position during the assembly process.

Accordingly, in at least some known processes, the electrode segments are fabricated from a contiguous ring that incorporates features that can be removed during a secondary process to generate the segmented electrode. The features may include narrow grooves cut into the inner diameter of the initial electrode at a depth that leaves just enough material to retain the contiguous circular profile on the outer diameter of the initial electrode. Once the initial electrode is integrated into the lead body, a centerless grinding process is utilized to remove the thin layer of Pt/Ir material that connecting the segments to one another.

The grooves may be formed using an EDM process that enables the formation of the grooves with very tight control. However, due to the small size of the electrodes and the grooves, the process takes time to complete, and requires careful removal of material, which can be costly. The thin flanges can be machined into the electrode tubing by removing material from the outer diameter of the tubing. This creates additional scrap of the Pt/Ir material, increasing costs (particularly at large volumes).

Accordingly, the systems and methods described herein facilitate providing more cost-effective techniques for manufacturing segmented electrodes. Two general concepts are described herein. The first utilizes progressive die stamping and coining processes to generate an initial electrode from a foil. The second uses machining and/or coining along with progressive die stamping to generate an initial electrode from a foil. The initial electrodes from either process are then segmented using a centerless grinding process to form the segmented electrode.

These processes reduce scrap and simplify formation of flange and groove features to reduce fabrication costs. Specifically, as described herein, the progressive die stamping and coining processes generate continuous flange and groove features without generating precious metal waste, and while simplifying fixturing and handling.

The methods described herein use a high volume progressive die and coining process to form foils into cylindrical electrodes that can be assembled onto lead bodies and segmented. In progressive die stamping, a foil is cut to a desired width and fed into a progressive die. The foil may be a roll or strip of material (e.g., Pt/Ir) having a sheet thickness that matches a desired electrode wall thickness. The machining operation can utilize EDM, but rather than process from the distal or proximal end of a ring electrode which is time-consuming, the EDM process would be performed on the face of the foil prior to progressive stamping.

As the foil is fed into the progressive die, the progressive die shapes the foil into the final desired form using a series of stamping and/or coining dies, with each die adding one or more features. When all the features have been added, the resulting part is separated from the progressive die and brought to a special forming die. The special forming die forms the part into a cylindrical geometry and locks the part in the cylindrical geometry using a junction method (e.g., laser welding). For a foil with pre-machined features present, specialized progressive stamping processes may be required to create the final cylindrical shape.

The benefits of such fabrication methods include reduced handling and registration of individual components, which is particularly beneficial for parts this small. The reduced handling enables faster processing times, which reduces the cost (in addition to the reduced amounts of precious metal required to form the features).

The following describes two general designs of segmented electrodes formed using progressive stamping techniques. However, those of skill in the art will appreciate that other suitable designs are possible using the systems and methods described herein.

Figure 3:
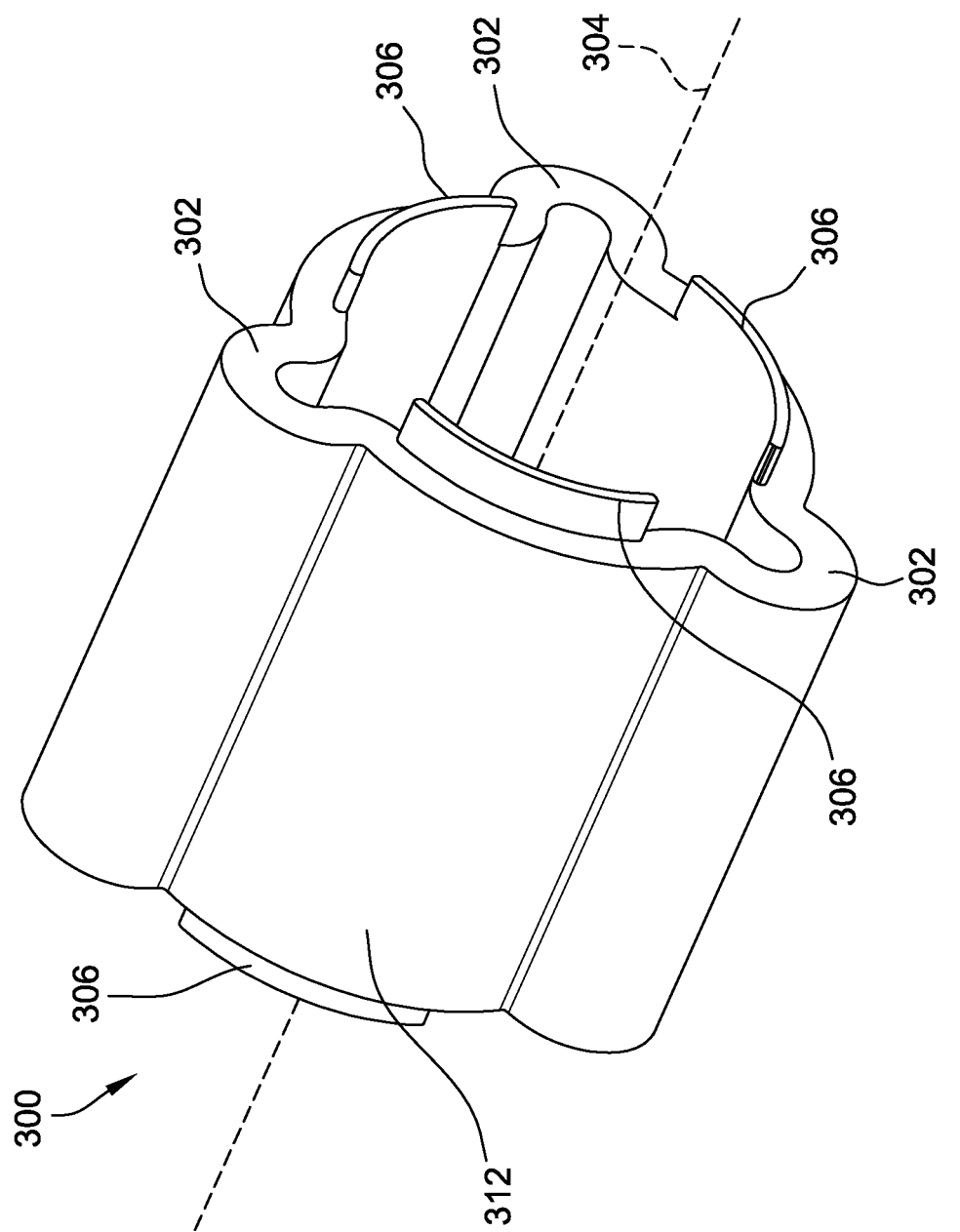
FIG. 3 is a perspective view of one embodiment of an initial electrode that may be formed using a progressive stamping technique.

FIG. 3 is a perspective view of one embodiment of an initial electrode 300 that may be formed using a progressive stamping technique. As described herein, initial electrode 300 is segmented into separate contacts to form a segmented electrode.

As shown in FIG. 3, initial electrode 300 is generally tubular, and includes a plurality of sacrificial tabs 302 that extend radially outward (i.e., outward from a longitudinal axis 304). Initial electrode 300 also includes a plurality of retaining tabs 306 that extend axially (i.e., along longitudinal axis 304) in proximal and distal directions. In some embodiments, retaining tabs 306 extend at least partially radially outward to facilitate aligning initial electrode 300 on a lead body.

In this embodiment, initial electrode 300 includes three sacrificial tabs 302, and six retaining tabs 306 (i.e., three pairs each including a proximal-extending retaining tab and a distal-extending retaining tab). Alternatively, initial electrode 300 may include any suitable number of sacrificial tabs 302 and retaining tabs 306.

As described in further detail below, initial electrode 300 is formed from a sheet of material. To form the annular shape of initial electrode, two ends of the sheet are joined together at a weld (not shown), for example, using laser welding. The weld may be located on one of sacrificial tabs 302. Alternatively, the weld may be located at another position on initial electrode 300.

Retaining tabs 306 may be generated using a coining process. Retaining tabs 306 enable securing the segmented electrode to a lead body. Specifically, retaining tabs 306 have a thinner wall than a contact body 312 from which they extend. This allows polymer of the lead body to be flowed over retaining tab 306 without covering contact body 312, securing contact body 312 to the lead body.

To segment initial electrode 300 into multiple contacts, sacrificial tabs 302 are removed from initial electrode 300 (e.g., using a centerless grinding process). This removal also eliminates weld 310 from the final segmented electrode. Accordingly, sacrificial tabs 302 may be relatively thin to facilitate minimizing the material wasted during the segmentation, and to facilitate minimizing gaps between the contacts in the segmented electrode. Removing the weld 310 as part of forming the final segmented electrode may be advantageous, as it ensures that the remaining components are identical and have the same clinical performance.

Notably, different fabrication methods may be combined to facilitate optimizing geometries and fabrication costs. For example, retaining tabs 306 may be created with a secondary machining processes (e.g., traditional machining or EDM) in some embodiments.

Figure 4:
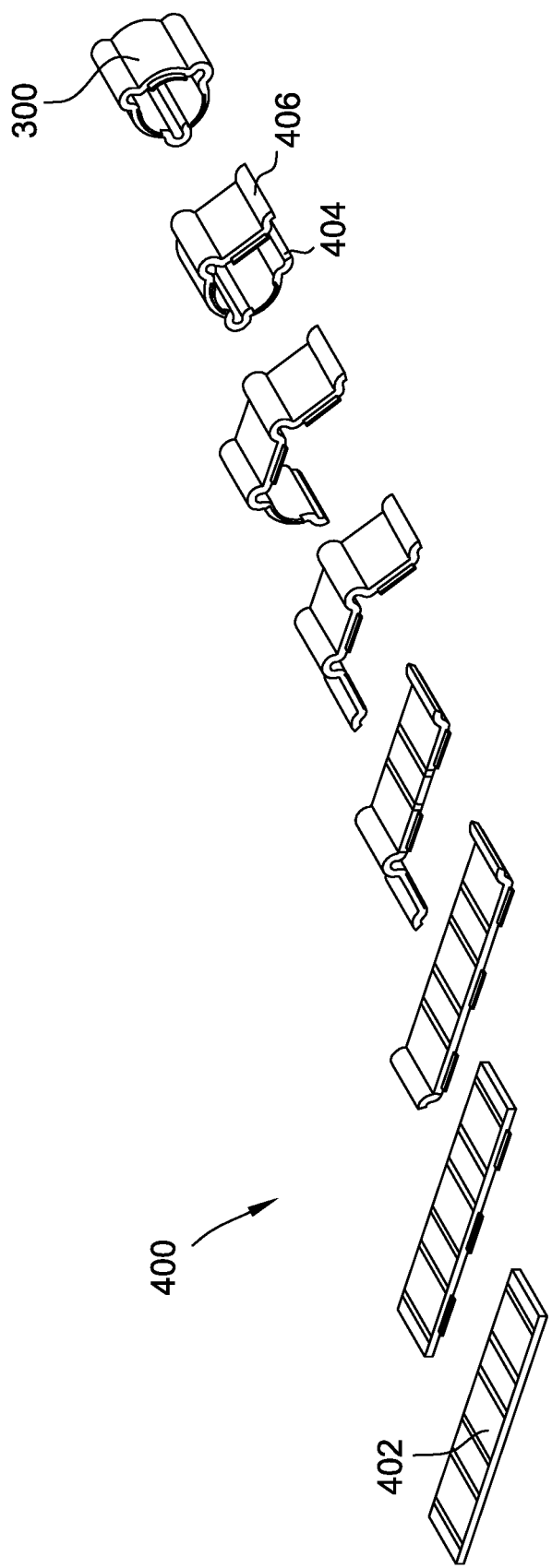
FIG. 4 is a diagram illustrating a sequence of progressive stamping steps that may be used to generate the initial electrode shown in FIG. 3.

FIG. 4 is a diagram illustrating a sequence 400 of progressive stamping steps that may be used to generate initial electrode 300 (shown in FIG. 3). As shown in FIG. 4, starting with a flat piece 402 of material (e.g., Pt/Ir), a coining operation is applied to form retaining tabs 306. Subsequently, stamping operations are applied to form small radius bends and then large radius bends (forming sacrificial tabs 302 and the general annular shape of initial electrode 300). Subsequently, two ends 404 and 406 of the formed geometry are welded together (e.g., using laser welding) to form weld 310 and secure the shape of initial electrode 300.

Figure 5B:
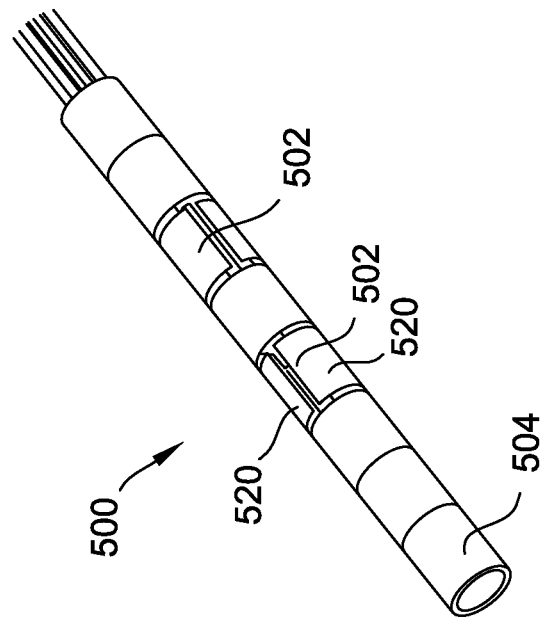
FIGS. 5A and 5B illustrate one embodiment of formation of an electrode assembly including two segmented electrodes on a lead body, with FIG. 5A showing the electrode assembly before a centerless grinding process and FIG. 5B showing the electrode assembly after the centerless grinding process.
Figure 5A:
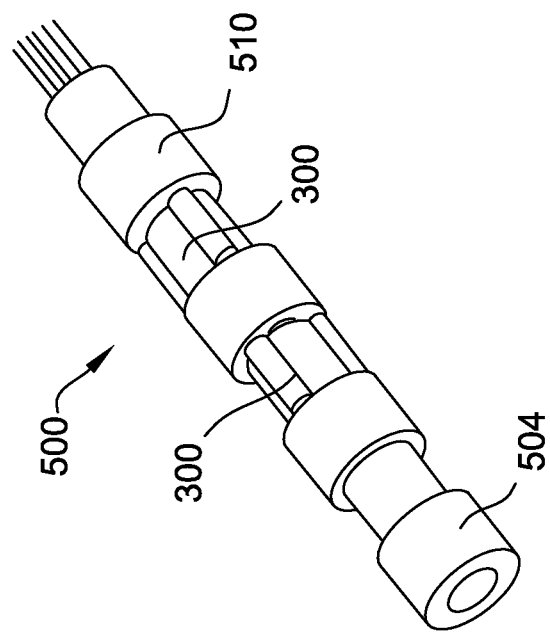

FIGS. 5A and 5B illustrate one embodiment of formation of an electrode assembly 500 including two segmented electrodes 502 on a lead body 504. FIG. 5A shows electrode assembly 500 before a centerless grinding process, and FIG. 5B shows electrode assembly 500 after the centerless grinding process.

As shown in FIG. 5A, two initial electrodes 300 are positioned on lead body 504. Retaining tabs 306 on each initial electrode 300 extend into polymer sections 510 of lead body 504. Notably, retaining tabs 306 may assist in fixing a positioning of initial electrode 300 during assembly of electrode assembly 500, making it easier to weld leads to what will ultimately become the contacts of segmented electrode 502. Retaining tabs 306 may also assist in positioning of initial electrodes 300 during the attachment of conductor wires to each of the internal faces of initial electrodes 300.

Molding and grinding operations are applied to lead body 504 and initial electrodes 300. These operations reduce the outer diameter of polymer sections 510, and remove sacrificial tabs 302 from each initial electrode 300, generating two segmented electrodes 502 each including a plurality of circumferentially spaced contacts 520.

Figure 6:
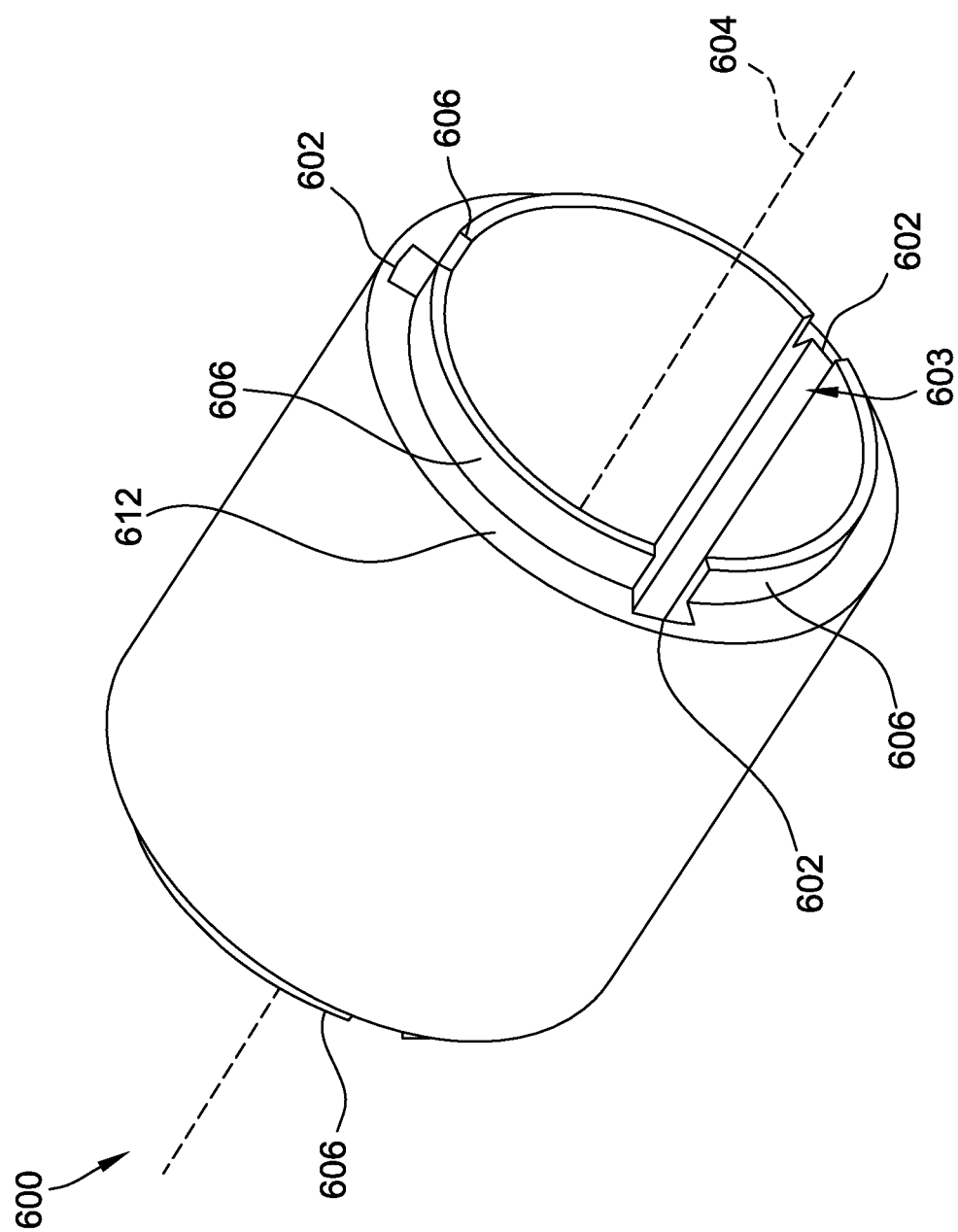
FIG. 6 is a perspective view of another embodiment of an initial electrode that may be formed using a progressive stamping technique.

FIG. 6 is a perspective view of another embodiment of an initial electrode 600 that may be formed using a progressive stamping technique. Like initial electrode 300 (shown in FIG. 3), initial electrode 600 may be segmented into separate contacts to form a segmented electrode.

As shown in FIG. 6, initial electrode 600 is substantially tubular, and includes a plurality of sacrificial sections 602. Unlike sacrificial tabs 302, sacrificial sections 602 have the same outer diameter as contact bodies 612 of initial electrode 600 (that will ultimately form the separate contacts of the segmented electrode), but have a larger inner diameter formed by a groove 603, resulting in a thin wall structure. Sacrificial sections 602 may be created during the progressive stamping process using coining. Alternatively, sacrificial sections 602 may be formed using traditional machining or EDM prior to the progressive stamping. Similar to initial electrode 300, centerless grinding may be used to remove sacrificial sections 602, segmenting initial electrode 600 into a plurality of circumferentially spaced contacts.

Initial electrode 600 also includes a plurality of retaining tabs 606 that extend axially (i.e., along a longitudinal axis 604) in proximal and distal directions. In some embodiments, retaining tabs 606 extend at least partially radially outward to facilitate aligning initial electrode 600 on a lead body.

In this embodiment, initial electrode 600 includes three sacrificial sections 602, and six retaining tabs 606 (i.e., three pairs each including a proximal-extending retaining tab and a distal-extending retaining tab). Alternatively, initial electrode 600 may include any suitable number of sacrificial sections 602 and retaining tabs 606. In this embodiment, initial electrode 600 is formed from a sheet of material, similar to initial electrode 300.

Retaining tabs 606 may be generated using a coining process. Retaining tabs 606 enable securing the segmented electrode to a lead body. Specifically, retaining tabs 606 have a thinner wall than a contact body 612 from which they extend. This allows polymer of the lead body to be flowed over retaining tab 606 without covering contact body 612, securing contact body 612 to the lead body.

To segment initial electrode 600 into multiple contacts, sacrificial sections 602 are removed from initial electrode 600 (e.g., using a centerless grinding process). Accordingly, sacrificial sections 602 may be relatively thin to facilitate minimizing the material wasted during the segmentation, and to facilitate minimizing gaps between the contacts in the segmented electrode.

Notably, different fabrication methods may be combined to facilitate optimizing geometries and fabrication costs. For example, retaining tabs 606 may be created with a secondary machining processes (e.g., traditional machining or EDM) in some embodiments.

The embodiments described herein facilitate fabricating directional electrodes in an efficient and economical manner. This includes reducing the fabrication time, reducing the amount of precious metal that is removed, simplifying the assembly process onto the lead body. Those of skill in the art will appreciate that there are many possible stamping and coining possibilities that can achieve these results beyond the examples specifically discussed herein. The dimensional control that the stamping and coining operation provide enable reducing how much previous metal has to be ground away to generate the individual segments. At least some known EDM processes may achieve very fine dimensional control, but the required fixturing and handling of the very small components in such processes may add significant time and cost to the process.

In some embodiment, other processes may be used to form the segments and retaining flanges using metal movement similar to the stamping/coining operations described herein. In such embodiments, the fabrication process may begin with a tube instead of a foil. For example, one option would be to swage down a tube over a custom mandrel that has stepped splines that create the segments (grooves in the inner diameter of the electrode). As another example, the tube could be drawn down over a custom mandrel that has stepped splines. With the internal grooves in place, the retaining flanges could be formed using coining or machining. These examples would eliminate the need to EDM the grooves in the inner diameter of the electrode and would eliminate the need for a weld.

The embodiments described herein provide systems and methods for fabricating a segmented electrode is provided. A method includes performing a series of progressive die stamping operations on a foil sheet of material to form an initial electrode, and removing portions of the initial electrode using a centerless grinding process to form a segmented electrode including a plurality of circumferentially spaced contacts.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A method for fabricating a segmented electrode, the method comprising:
performing a series of progressive die stamping operations on a foil sheet of material to form an initial electrode, wherein the initial electrode includes i) a plurality of contact bodies having a first thickness and ii) at least one retaining tab extending axially from each contact body, the at least one retaining tab having a same inner diameter as the plurality of contact bodies and having a second thickness smaller than the first thickness; and removing portions of the initial electrode using a centerless grinding process to form a segmented electrode including a plurality of circumferentially spaced contacts.

2. The method of claim 1, wherein performing a series of progressive die stamping operations comprises performing a coining operation to form the at least one retaining tab.

3. The method of claim 2, wherein the at least one retaining tab includes a first retaining tab extending axially in a proximal direction from an associated contact body and a second retaining tab extending axially in a distal direction from the associated contact body.

4. The method of claim 1, wherein performing a series of progressive die stamping operations comprises performing a stamping operation to form a plurality of sacrificial tabs on the initial electrode, the plurality of sacrificial tabs extending radially outward.

5. The method of claim 4, further comprising forming a weld on one of the plurality of sacrificial tabs.

6. The method of claim 4, wherein removing portions of the initial electrode comprises removing the plurality of sacrificial tabs.

7. The method of claim 1, wherein performing a series of progressive die stamping operations comprises performing a stamping operation to form a plurality of sacrificial sections on the initial electrode, the sacrificial sections having the same outer diameter as the contact bodies of the initial electrode.

8. The method of claim 7, wherein removing portions of the initial electrode comprises removing the plurality of sacrificial tabs.

9. The method of claim 1, wherein the initial electrode includes three sacrificial sections and three retaining tabs.

10. The method of claim 1, wherein the foil sheet of material is a foil sheet of a platinum-iridium alloy, a different allow, or pure platinum.

11. A method of forming an electrode assembly, the method comprising:
performing a series of progressive die stamping operations on a foil sheet of material to form an initial electrode, wherein the initial electrode includes i) a plurality of contact bodies having a first thickness and ii) at least one retaining tab extending axially from each contact body, the at least one retaining tab having a same inner diameter as the plurality of contact bodies and having a second thickness smaller than the first thickness;
coupling the initial electrode to a lead body; and
removing portions of the initial electrode using a centerless grinding process to form a segmented electrode on the lead body, the segmented electrode including a plurality of circumferentially spaced contacts.

12. The method of claim 11, wherein performing a series of progressive die stamping operations comprises performing a coining operation, a traditional machining operation, or an electrical discharge machining operation to form the at least one retaining tab.

13. The method of claim 12, wherein the at least one retaining tab includes a first retaining tab extending axially in a proximal direction from an associated contact body and a second retaining tab extending axially in a distal direction from the associated contact body.

14. The method of claim 11, wherein performing a series of progressive die stamping operations comprises performing a stamping operation to form a plurality of sacrificial tabs on the initial electrode, the plurality of sacrificial tabs extending radially outward.

15. The method of claim 14, further comprising forming a weld on one of the plurality of sacrificial tabs.

16. The method of claim 14, wherein removing portions of the initial electrode comprises removing the plurality of sacrificial tabs.

17. The method of claim 11, wherein performing a series of progressive die stamping operations comprises performing a stamping operation to form a plurality of sacrificial sections on the initial electrode, the sacrificial sections having the same outer diameter as the contact bodies of the initial electrode.

18. The method of claim 17, wherein removing portions of the initial electrode comprises removing the plurality of sacrificial tabs.

19. The method of claim 11, wherein the initial electrode includes three sacrificial sections and three retaining tabs.

20. The method of claim 11, wherein coupling the initial electrode to a lead body comprises flowing a polymer of the lead body over the at least one retaining tab.

21. A method of forming an implantable stimulation lead, the method comprising:
performing a series of progressive die stamping operations on a foil sheet of material to form an initial electrode, wherein the initial electrode includes i) a plurality of contact bodies having a first thickness and ii) at least one retaining tab extending axially from each contact body, the at least one retaining tab having a same inner diameter as the plurality of contact bodies and having a second thickness smaller than the first thickness;
coupling the initial electrode to a lead body;
removing portions of the initial electrode using a centerless grinding process to form a segmented electrode on the lead body, the segmented electrode including a plurality of circumferentially spaced contacts; and
electrically connecting each of the plurality of circumferentially spaced contacts to associated conductors of the lead body to form the implantable stimulation lead.

22. The method of claim 21, further comprising electrically connecting the plurality of circumferentially spaced contacts to respective terminals of the lead body, each circumferentially spaced contact electrically connected to the respective terminal by the associated conductor.

23. The method of claim 21, wherein performing a series of progressive die stamping operations comprises performing a coining operation to form the at least one retaining tab.

24. The method of claim 21, wherein performing a series of progressive die stamping operations comprises performing a stamping operation to form a plurality of sacrificial tabs on the initial electrode, the plurality of sacrificial tabs extending radially outward.

* * * * *